(12) United States Patent
DeCarlo

(10) Patent No.: US 9,486,269 B2
(45) Date of Patent: Nov. 8, 2016

(54) ELECTROSURGICAL SYSTEMS AND CARTRIDGES FOR USE THEREWITH

(75) Inventor: Arnold V. DeCarlo, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 2064 days.

(21) Appl. No.: 11/821,361

(22) Filed: Jun. 22, 2007

(65) Prior Publication Data

US 2008/0319438 A1 Dec. 25, 2008

(51) Int. Cl.
| | | |
|---|---|---|
| A61B 18/12 | (2006.01) | |
| A61B 18/14 | (2006.01) | |
| A61B 18/00 | (2006.01) | |
| A61B 18/18 | (2006.01) | |

(52) U.S. Cl.
CPC ............. A61B 18/12 (2013.01); A61B 18/14 (2013.01); *A61B 18/1477* (2013.01); *A61B 18/18* (2013.01); *A61B 2018/00023* (2013.01); *A61B 2018/00166* (2013.01); *A61B 2018/00172* (2013.01); *A61B 2018/00178* (2013.01); *A61B 2018/1425* (2013.01)

(58) Field of Classification Search
CPC .. A61B 18/082; A61B 18/085; A61B 18/14; A61B 2018/00005; A61B 2018/00011; A61B 2018/00166; A61B 2018/00172; A61B 2018/00178; A61B 2018/0091
USPC ............... 606/1, 20–52; 128/898; 433/77–79
See application file for complete search history.

(56) References Cited

U.S. PATENT DOCUMENTS

| | | | |
|---|---|---|---|
| 2,031,682 A | | 2/1936 | Frederick et al. |
| 3,825,004 A | * | 7/1974 | Durden, III ............. 604/20 |
| 4,074,718 A | | 2/1978 | Morrison, Jr. et al. |
| 4,151,648 A | * | 5/1979 | Hirth ...................... 433/78 |
| 4,231,737 A | * | 11/1980 | Groen ............... A61G 15/16 433/78 |
| 4,259,066 A | * | 3/1981 | Pietschmann ............ 433/78 |
| 4,375,220 A | | 3/1983 | Matvias |
| 4,411,266 A | | 10/1983 | Cosman |
| 4,526,175 A | * | 7/1985 | Chin et al. ................ 606/192 |
| 4,565,200 A | | 1/1986 | Cosman |
| 4,576,177 A | | 3/1986 | Webster, Jr. |
| 4,608,977 A | | 9/1986 | Brown |
| 4,662,383 A | | 5/1987 | Sogawa et al. |
| 4,739,759 A | | 4/1988 | Rexworth et al. |

(Continued)

FOREIGN PATENT DOCUMENTS

| | | |
|---|---|---|
| DE | 2407559 | 2/1974 |
| DE | 10224154 | 12/2003 |

(Continued)

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.

(Continued)

*Primary Examiner* — Ronald Hupczey, Jr.

(57) ABSTRACT

A cartridge for use with an electrosurgical system includes a housing, a conduit, and a conductor. The housing includes a path defined therein. The conduit is disposed at least partially within the housing such that the path is configured to position at least a portion of the conduit within the housing. A chamber of the path is configured to dampen shock forces on the conduit. The conductor is adapted to transmit energy is disposed within the housing. At least a portion of the conductor is disposed at least partially within the housing.

14 Claims, 3 Drawing Sheets

(56) References Cited

U.S. PATENT DOCUMENTS

| | | | |
|---|---|---|---|
| 4,832,024 A | 5/1989 | Boussignac et al. | |
| 4,880,719 A | 11/1989 | Murofushi et al. | |
| 4,961,435 A | 10/1990 | Kitagawa et al. | |
| 4,966,597 A | 10/1990 | Cosman | |
| 4,993,430 A | 2/1991 | Shimoyama et al. | |
| 5,029,588 A | 7/1991 | Yock et al. | |
| 5,103,804 A | 4/1992 | Abele et al. | |
| 5,225,741 A | 7/1993 | Auld et al. | |
| 5,230,623 A | 7/1993 | Guthrie et al. | |
| 5,233,515 A | 8/1993 | Cosman | |
| 5,246,438 A | 9/1993 | Langberg | |
| 5,254,117 A * | 10/1993 | Rigby et al. | 606/46 |
| 5,256,138 A * | 10/1993 | Burek et al. | 606/42 |
| 5,267,994 A | 12/1993 | Gentelia et al. | |
| 5,281,213 A | 1/1994 | Milder et al. | |
| 5,297,961 A * | 3/1994 | Hanson | A61G 15/16 433/77 |
| 5,323,778 A | 6/1994 | Kandarpa et al. | |
| 5,330,470 A | 7/1994 | Hagen | |
| 5,330,518 A | 7/1994 | Nielson et al. | |
| 5,334,193 A | 8/1994 | Nardella | |
| 5,342,357 A | 8/1994 | Nardella | |
| 5,348,554 A | 9/1994 | Imran et al. | |
| 5,370,675 A | 12/1994 | Edwards et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A | 4/1995 | Abele et al. | |
| 5,409,000 A | 4/1995 | Imran | |
| 5,409,006 A | 4/1995 | Buchholtz et al. | |
| 5,417,686 A | 5/1995 | Peterson et al. | |
| 5,425,634 A * | 6/1995 | Brockway | A61C 1/0061 433/28 |
| 5,433,739 A | 7/1995 | Sluijter et al. | |
| 5,437,662 A | 8/1995 | Nardella | |
| 5,458,597 A | 10/1995 | Edwards et al. | |
| 5,462,521 A | 10/1995 | Brucker et al. | |
| 5,472,441 A | 12/1995 | Edwards et al. | |
| 5,490,850 A | 2/1996 | Ellman et al. | |
| 5,500,012 A | 3/1996 | Brucker et al. | |
| 5,520,684 A | 5/1996 | Imran | |
| 5,536,267 A | 7/1996 | Edwards et al. | |
| 5,554,112 A * | 9/1996 | Walbrink | A61B 18/1482 604/119 |
| 5,571,147 A | 11/1996 | Sluijter et al. | |
| 5,588,432 A | 12/1996 | Crowley | |
| 5,599,345 A | 2/1997 | Edwards et al. | |
| 5,643,197 A | 7/1997 | Brucker et al. | |
| 5,647,871 A | 7/1997 | Levine et al. | |
| 5,662,111 A | 9/1997 | Cosman | |
| 5,688,267 A | 11/1997 | Panescu et al. | |
| 5,735,847 A | 4/1998 | Gough et al. | |
| 5,775,338 A | 7/1998 | Hastings | |
| 5,792,139 A * | 8/1998 | Chambers | A61B 18/1482 606/41 |
| 5,792,146 A | 8/1998 | Cosman | |
| 5,827,292 A * | 10/1998 | Anis | 606/107 |
| 5,848,967 A | 12/1998 | Cosman | |
| 5,849,011 A | 12/1998 | Jones et al. | |
| 5,868,740 A | 2/1999 | LeVeen et al. | |
| 5,921,982 A | 7/1999 | Lesh et al. | |
| 5,943,719 A | 8/1999 | Feldman et al. | |
| 5,951,546 A | 9/1999 | Lorentzen | |
| 6,001,093 A | 12/1999 | Swanson et al. | |
| 6,006,126 A | 12/1999 | Cosman | |
| 6,013,048 A * | 1/2000 | Podany et al. | 604/22 |
| 6,053,912 A | 4/2000 | Panescu et al. | |
| 6,059,780 A | 5/2000 | Gough et al. | |
| 6,061,551 A | 5/2000 | Sorrells et al. | |
| 6,074,389 A | 6/2000 | Levine et al. | |
| 6,080,149 A | 6/2000 | Huang et al. | |
| 6,106,524 A | 8/2000 | Eggers et al. | |
| 6,132,426 A | 10/2000 | Kroll | |
| 6,146,380 A | 11/2000 | Racz et al. | |
| 6,162,216 A | 12/2000 | Guziak et al. | |
| 6,203,541 B1 | 3/2001 | Keppel | |
| 6,217,328 B1 * | 4/2001 | Oliver | A61C 1/0084 433/29 |
| 6,241,725 B1 | 6/2001 | Cosman | |
| 6,246,912 B1 | 6/2001 | Sluijter et al. | |
| 6,287,305 B1 | 9/2001 | Heim et al. | |
| 6,306,132 B1 | 10/2001 | Moorman et al. | |
| 6,337,998 B1 | 1/2002 | Behl et al. | |
| 6,432,070 B1 | 8/2002 | Talish et al. | |
| 6,478,793 B1 | 11/2002 | Cosman et al. | |
| 6,500,172 B1 | 12/2002 | Panescu et al. | |
| 6,506,189 B1 | 1/2003 | Rittman, III et al. | |
| 6,530,922 B2 | 3/2003 | Cosman et al. | |
| 6,575,969 B1 | 6/2003 | Rittman, III et al. | |
| 6,605,085 B1 | 8/2003 | Edwards | |
| 6,613,047 B2 | 9/2003 | Edwards | |
| 6,685,729 B2 | 2/2004 | Gonzalez | |
| 7,137,980 B2 | 11/2006 | Buysse et al. | |
| 7,156,842 B2 | 1/2007 | Sartor et al. | |
| 7,179,255 B2 | 2/2007 | Lettice et al. | |
| 7,186,222 B1 * | 3/2007 | Callister et al. | 600/549 |
| 7,207,989 B2 | 4/2007 | Pike, Jr. et al. | |
| 7,218,958 B2 | 5/2007 | Rashidi | |
| 7,235,070 B2 | 6/2007 | Vanney | |
| 7,235,073 B2 | 6/2007 | Levine et al. | |
| 7,238,184 B2 | 7/2007 | Megerman et al. | |
| 7,264,619 B2 | 9/2007 | Venturelli | |
| 7,278,991 B2 | 10/2007 | Morris et al. | |
| 7,294,127 B2 | 11/2007 | Leung et al. | |
| 7,294,143 B2 | 11/2007 | Francischelli | |
| 7,302,285 B2 | 11/2007 | Fuimaono et al. | |
| 7,303,558 B2 | 12/2007 | Swanson | |
| 7,331,947 B2 * | 2/2008 | McGuckin et al. | 604/506 |
| RE40,156 E | 3/2008 | Sharps et al. | |
| 7,341,586 B2 | 3/2008 | Daniel et al. | |
| 7,344,533 B2 | 3/2008 | Pearson et al. | |
| 7,364,578 B2 | 4/2008 | Francischelli et al. | |
| 7,364,579 B2 | 4/2008 | Mulier et al. | |
| 7,367,974 B2 | 5/2008 | Haemmerich et al. | |
| 7,367,975 B2 | 5/2008 | Malecki et al. | |
| 7,387,625 B2 | 6/2008 | Hovda et al. | |
| 7,419,486 B2 | 9/2008 | Kampa | |
| 7,419,487 B2 | 9/2008 | Johnson et al. | |
| 7,419,488 B2 | 9/2008 | Ciarrocca et al. | |
| 7,419,489 B2 | 9/2008 | Vanney et al. | |
| 7,422,587 B2 | 9/2008 | Bek et al. | |
| 7,871,395 B2 * | 1/2011 | Hu et al. | 604/96.01 |
| 2001/0034518 A1 | 10/2001 | Edwards et al. | |
| 2002/0058933 A1 | 5/2002 | Christopherson et al. | |
| 2002/0111615 A1 | 8/2002 | Cosman et al. | |
| 2002/0120261 A1 | 8/2002 | David et al. | |
| 2002/0156472 A1 | 10/2002 | Lee et al. | |
| 2003/0018247 A1 | 1/2003 | Gonzalez | |
| 2004/0002745 A1 | 1/2004 | Fleming et al. | |
| 2004/0030330 A1 * | 2/2004 | Brassell | A61B 18/1206 606/41 |
| 2004/0039429 A1 | 2/2004 | Daniel et al. | |
| 2004/0181216 A1 * | 9/2004 | Kelly et al. | 606/41 |
| 2004/0199161 A1 | 10/2004 | Truckai et al. | |
| 2004/0254573 A1 | 12/2004 | Dycus | |
| 2004/0267256 A1 | 12/2004 | Garabedian et al. | |
| 2005/0096681 A1 | 5/2005 | Desinger et al. | |
| 2005/0107784 A1 | 5/2005 | Moses | |
| 2005/0107785 A1 | 5/2005 | Dycus | |
| 2005/0113824 A1 | 5/2005 | Sartor et al. | |
| 2005/0119655 A1 | 6/2005 | Moses | |
| 2005/0154387 A1 | 7/2005 | Moses | |
| 2005/0155743 A1 | 7/2005 | Getz, Jr. et al. | |
| 2005/0192564 A1 | 9/2005 | Cosman et al. | |
| 2006/0079885 A1 | 4/2006 | Rick et al. | |
| 2006/0079886 A1 | 4/2006 | Orszulak | |
| 2006/0079887 A1 | 4/2006 | Buysse | |
| 2007/0066971 A1 | 3/2007 | Podhajsky | |
| 2007/0073285 A1 | 3/2007 | Peterson | |
| 2007/0078453 A1 | 4/2007 | Johnson | |
| 2007/0078454 A1 | 4/2007 | McPherson | |
| 2007/0260240 A1 | 11/2007 | Rusin | |

(56) References Cited

U.S. PATENT DOCUMENTS

| | | | |
|---|---|---|---|
| 2008/0021448 A1 | 1/2008 | Orszulak | |
| 2008/0027424 A1 | 1/2008 | DeCarlo et al. | |
| 2008/0183165 A1 | 7/2008 | Buysse et al. | |

FOREIGN PATENT DOCUMENTS

| | | |
|---|---|---|
| EP | 0171967 A | 2/1986 |
| EP | 0246350 | 11/1987 |
| EP | 0310431 | 4/1989 |
| EP | 0608609 | 8/1994 |
| EP | 1070518 A2 | 1/2001 |
| EP | 1465037 A | 10/2004 |
| EP | 1645234 | 4/2006 |
| EP | 1656900 | 5/2006 |
| FR | 2864439 | 7/2005 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 99/01074 | 1/1999 |
| WO | WO 99/04710 | 2/1999 |
| WO | WO 99/22657 | 5/1999 |
| WO | WO 00/67846 | 11/2000 |
| WO | WO 01/00114 A1 | 1/2001 |
| WO | WO 2004/045436 | 6/2004 |
| WO | WO 2005/009528 | 2/2005 |

OTHER PUBLICATIONS

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedence", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et al., "Image-guided Radiofrequency Tumor Ablation: Challenges and Opportunities—Part I", (2001) *J Vasc. Interv. Radial*, vol. 12, pp. 1021-1032.

McGahan et al. (1995) "Percutaneous Ultrasound-guided Radiofrequency Electrocautery Ablationof Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

Bulletin of the American Physical Society, vol. 47, No. 5, Aug. 2002.

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

European Search Report from Application EP 05025423.4 dated Jan. 12, 2007.

European Search Report from Application EP 06019768 dated Jan. 8, 2007.

European Search Report from Application EP 05025424 dated Jan. 23, 2007.

European Search Report from Application EP 07009028 dated Jul. 16, 2007.

McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

\* cited by examiner

ELECTROSURGICAL SYSTEMS AND CARTRIDGES FOR USE THEREWITH

BACKGROUND

1. Technical Field

The present disclosure relates generally to cartridges for use with an electrosurgical system and, more particularly, to cartridges configured to receive conductors and conduits of an electrosurgical system.

2. Background of the Related Art

Electrosurgical systems are well known in the art. Some electrosurgical systems employ microwave energy to produce a number of therapeutic effects in or on tissue at a target surgical site during any number of surgical procedures. Many electrosurgical systems transmit microwave energy as well as other kinds of energy through conductors, such as, wires, cables, tubing or other suitable energy transmission structures. In addition to the energy transmitting conductors, some electrosurgical systems have conduits adapted to carry cooling fluids to the surgical tip of the electrosurgical system. These conduits transport cooling fluid to the surgical tip of the electrosurgical system to transfer heat between the surgical tip and the fluid within the conduit.

The process of connecting the conduits and/or conductors to the electrosurgical system is often cumbersome. Ideally, a user should be able to easily connect the conduits and conductors to the electrosurgical system.

SUMMARY

The present disclosure relates to a cartridge for use with an electrosurgical system where the cartridge includes a housing, a conduit, and a conductor. The housing includes a path. The conduit is disposed at least partially within the housing such that the path is configured to position at least a portion of the conduit within the housing. A portion of the path is configured to dampen shock forces on the conduit. The conductor is adapted to transmit energy. A portion of the conductor is disposed at least partially within the housing.

The present disclosure also relates to a cartridge having a housing for use with an electrosurgical system where a path in the housing is configured to position at least a portion of a conduit and at least a portion of a conductor within the housing. A chamber of the path is configured to dampen shock forces on at least a portion of the conduit disposed in mechanical cooperation therewith.

Further still, the present disclosure relates to an electrosurgical system comprising a surgical instrument, a conductor, a conduit, a cartridge, a pump, and a generator. The conduit is disposed in mechanical cooperation with the surgical instrument. The conductor is disposed in mechanical cooperation with the surgical instrument. The cartridge includes a path and is configured to position at least a portion of the conduit and at least a portion of the conduit. A chamber of the path is configured to dampen shock forced on the conduit. A pump is disposed in mechanical cooperation with a portion of the conduit. A generator is disposed in electro-mechanical cooperation with at portion of the conductor.

BRIEF DESCRIPTION OF THE DRAWINGS

Embodiments of the presently disclosed electrosurgical systems and cartridges for use therewith are disclosed herein with reference to the drawings, wherein.

DETAILED DESCRIPTION OF THE EMBODIMENTS

Figure 1:
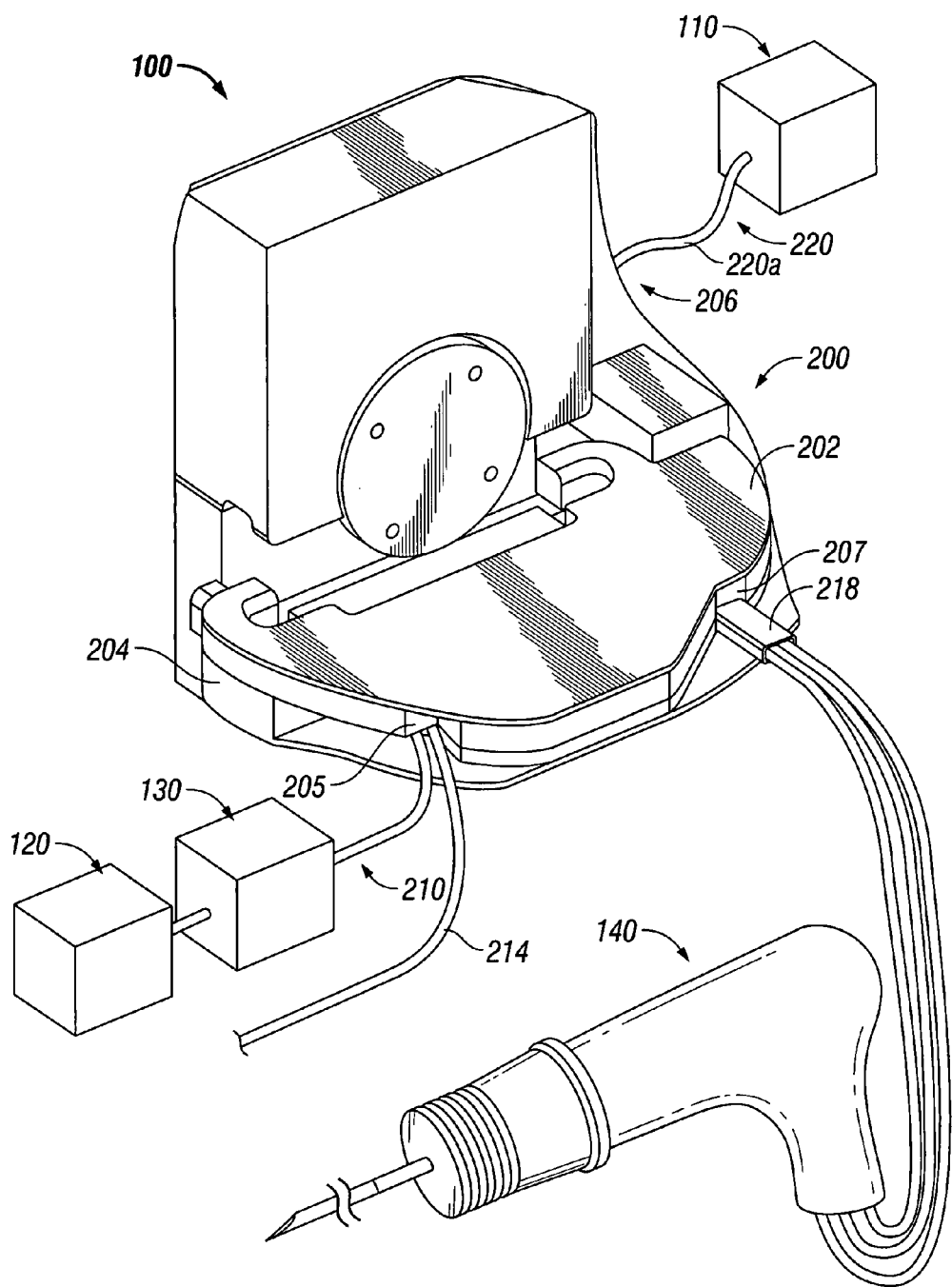
FIG. 1 is a schematic view of an electrosurgical system having a cartridge according to an embodiment of the present disclosure.

Embodiments of the presently disclosed electrosurgical systems and cartridges for use therewith are described in detail with reference to the drawings, in which like reference numerals designate identical or corresponding elements in each of the several views. As used herein and as is traditional, the term "distal" refers to the portion that is farther from the user and the term "proximal" refers to the portion that is closer the user. Also, in the specification and the claims, all singular forms, including "a," "an," and "the," include the plural reference unless the context clearly dictates otherwise. Likewise, all plural forms include the singular reference.

The cartridge of the present disclosure is intended to be used with an electrosurgical system or any other suitable surgical system. Generally, electrosurgical systems deliver electrosurgical energy to tissue for thermal treatment such as tissue ablation, tissue vaporization, and tissue coagulation. For example, radio frequency (RF) energy may be applied to tissue to treat benign prostatic hyperplasia (BPH). The applications of electrosurgical systems, however, are not limited to the treatment of BPH. Surgeons often employ electrosurgical systems in other kinds of surgical procedures such as cardiac ablation, cancer treatment, among others. Some electrosurgical systems are designed for use during minimally invasive procedures.

The present disclosure relates to a cartridge for use with an electrosurgical system. The presently disclosed cartridge simplifies the assembly of an electrosurgical system. In particular, the configuration of the cartridge allows a user to easily connect conduits and conductors in an electrosurgical system. The structural arrangement of the cartridge also dampens the shock forces exerted on portions of the conduits by a liquid being pumped through the conduit, thereby reducing the stress on portions of the conduits.

Figure 2:
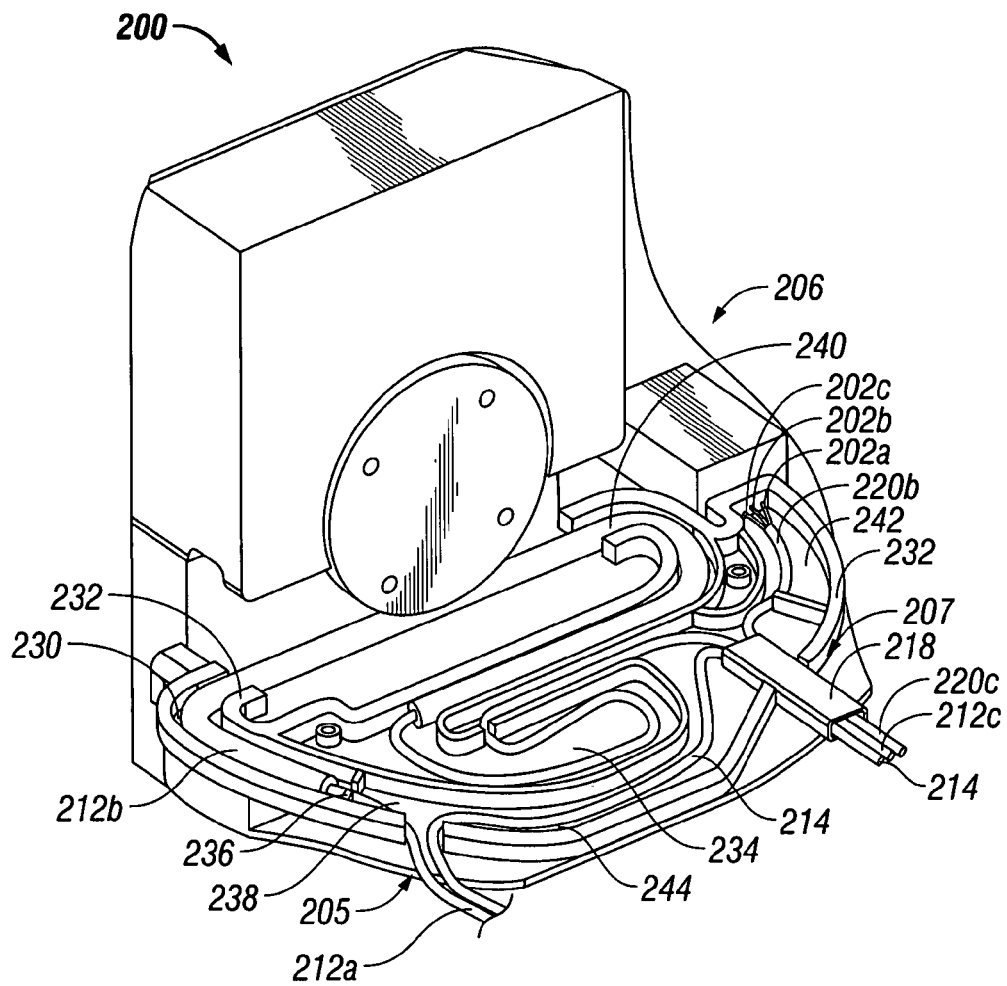
FIG. 2 is a perspective view of the cartridge of FIG. 1 with a portion of its cover detached.

Referring initially to FIGS. 1 and 2, an electrosurgical system is generally designated as reference numeral 100. The present disclosure is not limited to any specific kind of electrosurgical system. Rather, electrosurgical system 100 can be a microwave ablation system, an RF system or any other suitable surgical system. Electrosurgical system 100 includes an electrosurgical generator 110, a fluid source 120, a pump 130, a surgical instrument 140, and a cartridge 200. Surgical instrument 140 can be any suitable surgical apparatus, such as an ablation instrument, a microwave antenna, or an RF probe.

Electrosurgical generator 110 supplies energy to surgical instrument 140 and is in electromechanical cooperation with a conductor 220. The energy supplied by electrosurgical generator 110 is carried towards surgical instrument 140 through conductor 220. Accordingly, conductor 220 is adapted to transmit electrosurgical energy therethrough and may extend between electrosurgical generator 110 and surgical instrument 140. Conductor 220 can be made of any suitable electrically conductive material. Additionally, it is contemplated that conductor 220 can be formed of wires, cables, or any suitable energy transmitting apparatus. Moreover, conductor 220 can include one or more energy transmitting apparatuses. In the embodiment depicted in FIG. 3, for example, conductor 220 includes three wires 202a, 202b, and 202c.

Conductor 220 can have a first section 220a electrically connected to electrosurgical generator 110, a second section 220b at least partially disposed within a housing 204 of cartridge 200, and a third section 220c electrically connected to surgical instrument 140. Second section 220b is configured to electro-mechanically couple first section 220a and third section 220c of conductor 220. A conductor fitting (not explicitly shown) may interconnect first and second sections 220a, 220b and another conductor fitting (not explicitly shown) may interconnect second and third sections 220b, 220c. An electrically insulative material, such as heat shrink, may cover and/or insulate the conductor fittings.

Electrosurgical system 100 further includes a conduit 210 in fluid communication with fluid source 120. Fluid source 120 stores a fluid (e.g., cooling fluid). In operation, pump 130 extracts cooling fluid from fluid source 120 and delivers it to surgical instrument 140 through conduit 210. Hence, pump 130 is operatively connected to fluid source 120. A person skilled in the art will recognize, however, that fluid source 120 can be in mechanical cooperation with any suitable fluid delivery device capable of moving a fluid from fluid source 120 to surgical instrument 140 through conduit 210.

Figure 3:
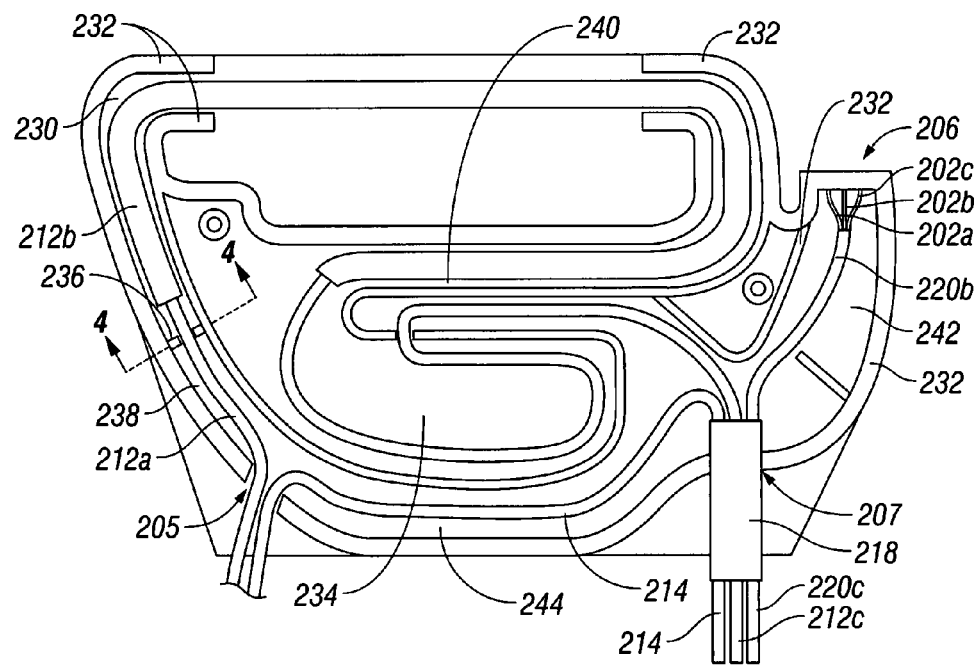
FIG. 3 is a top view of a portion of the cartridge of FIG. 1 with its cover detached.

Referring to FIG. 3, conduit 210 is adapted to carry cooling fluid and is at least partially disposed within housing 204 of cartridge 200. The present disclosure contemplates that conduit 210 may be a closed fluid channel. In particular, conduit 210 can include an inflow section 212 and an outflow section 214. Inflow section 212 of conduit 210 carries cooling fluid from fluid source 120 to surgical instrument 140 while outflow section 214 of conduit 210 carries cooling fluid away from surgical instrument 140. During operation, fluid source 120 supplies cooling fluid to inflow section 212 of conduit 210, the cooling fluid then flows through inflow section 212 of conduit 210 towards surgical device 140 and extracts or transfers at least part of the heat generated from surgical instrument 140, and thereafter, the cooling fluid flows away from surgical instrument 140 through outflow section 214 of conduit 210.

In the illustrated embodiment, inflow section 212 includes a first portion 212a operatively attached to fluid source 120, a second portion 212b at least partially disposed within housing 204, and a third portion 212b operatively connected to surgical instrument 140. Second portion 212a of inflow section 212 is configured to couple first and third portions 212a, 212c of inflow section 212. A conduit fitting 216 may interconnect first and second portions 212a, 212b of inflow section 212, as illustrated in FIG. 3. Those skilled in the art will recognize that conduit fitting 216 can be a luer fitting or any other suitable fitting. Conduit fitting 216 is disposed within housing 204 of cartridge 200. Cartridge 200 can include an additional conduit fitting (not explicitly shown) that interconnects second portion 212b and third portion 212c of inflow section 212. This conduit fitting may be disposed adjacent to the conductor fitting that interconnects second section 220b and third section 220c of conductor 220. All the fittings disclosed in the present disclosure can be positioned within housing 204 externally of housing 204, or partially within housing 204.

In addition to housing 204, cartridge 200 includes a first opening 205, a second opening 206, a third opening 207, and a cover 202 (See FIG. 1). First opening 205 is configured to receive a portion of inflow and/or outflow sections 212, 214 of conduit 210 while second opening 206 is adapted to receive a portion of conductor 220. Third opening 207 is configured to receive a portion of inflow and outflow sections 212, 214 of conduit 210, and a portion of conductor 220. In the illustrated embodiment, the portions of conduit 210 and conductor 220 that are contiguous to third opening 207 are contained with a sheath 218. At least a portion of sheath 218 is shown within housing 204. Sheath 218 can be made of an electrically and/or thermally insulative material. First, second, and third openings 205, 206, 207 can be located on housing 204, on cover 202, or can encompass an area including both cover 202 and housing 204.

Cover 202 of cartridge 200 is detachably attached to housing 204. When cover 202 is detached from housing 204 of cartridge 200, the internal components of cartridge 202 are accessible to a user, as shown in FIG. 3. Although the drawings show cover 202 sealing the entire housing 204, it is envisioned that cover 202 may seal only a portion of housing 204.

Figure 4:
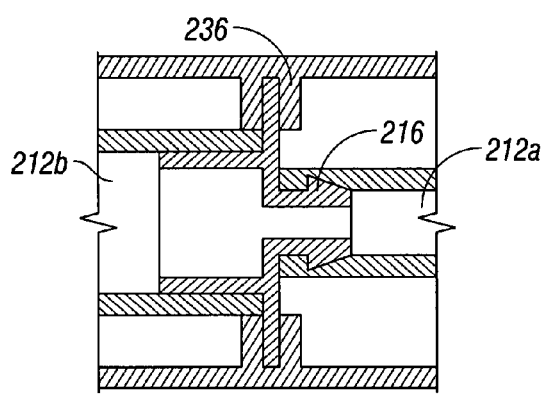
FIG. 4 is a sectional view of the cartridge of FIG. 3, taken through line 4-4 (shown in FIG. 3).

With reference to FIGS. 3 and 4, housing 204 of cartridge 200 includes a path 230 configured to position portions of conduit 210 and portions of conductor 220. Path 230, or a portion thereof, is configured to dampen shock forces exerted on conduit 210. As discussed above, pumping of liquid through conduit 210 can produce shock forces on conduit 210. As a result, conduit 210 may experience stress at least along a portion of its length. Pumping liquid through conduit 210 can also move conduit 210 within housing 204 of cartridge 200.

Path 230 includes a plurality of spaced apart walls 232 that can restrict the movement of at least a portion of conduit 210 within housing 204. Walls 232 may also isolate conduit 210 from conductor 220. At least a portion of conduit 210 is slidably disposed within path 230. In one embodiment, a portion of conduit 210 is positioned between a portion of walls 232. Path 230 further includes a chamber 234. Chamber 234 is configured to dampen the shock forces on conduit 210, e.g., by allowing slack of conduit 210 therein. Specifically, chamber 234 is configured to house portions of conduit 210 within cartridge 200 such that at least a portion of conduit 210 is not held tight, i.e., chamber 234 allows at least a portion of conduit 210 to deflect therein. More specifically and as illustrated in FIGS. 2 and 3, a width of chamber 234 is at least two times larger than a width of a portion conduit 210 positioned therein. Further, at least a portion of chamber 234 is configured to allow conduit 210 to move in a direction substantially perpendicular to a length of conduit 210 at a distance of at least twice the width of conduit 210. Consequently, when pumping liquid through conduit 210, conduit 210 is able to slide through path 230 due to the space provided for slack in chamber 234. This movement of conduit 210 may help reduce the stress and may help dampen shock forces on conduit 210.

As seen in FIG. 4, cartridge 200 additionally includes rib walls 236 positioned with housing 204. Rib walls 236 can be disposed in path 230, and are configured to receive and axially fix conduit fitting 216. Additionally, rib walls 236 are adapted to dampen shock forces on the conduit 210.

As shown in FIG. 3, walls 232 of path 230 define a first trail 238 adapted to receive at least a portion of inflow section 212 of conduit 210. This portion of inflow section 212 is slidably disposed in first trail 238. First trail 238 extends from first opening 205 of cartridge 100 to chamber 234 of housing 204. As discussed above, walls 230 also define a chamber 234 that is adapted to allow slack of inflow section 212 of conduit 210. Additionally, walls 232 of path 230 define a second trail 240. Second trail 240 extends from chamber 234 of housing 204 to third opening 207. A portion of inflow section 212 of conduit 210 is slidably disposed in second trail 240.

A third trail 242 is defined by walls 232 of path 230. A portion of conductor 220 is disposed in third trail 242. Third trail 242 extends from second opening 206 to third opening 207 of housing 204. First and second trails 238, 240 are shown separated from third trail 242 so that inflow section 212 of conduit 210 is isolated from conductor 220. This configuration may help reduce heat transfer between the cooling fluid in inflow section 212 and conductor 220 inside housing 204.

Walls 232 of path 230 define a fourth trail 244 configured to receive a portion of outflow section 214 of conduit 210. Fourth trail 244 extends from third opening 207 to first opening 205 of housing 204. Fourth trail 244 is shown separated from first, second, and third trails 238, 240, 242.

To assemble electrosurgical system 100, a user can couple conduit 210 to cartridge 100 and couple conduit 210 to surgical instrument 140. Conduit 210 can be connected to fluid source 120. Additionally, conductor 220 can be connected to electrosurgical generator 110 and cartridge 100.

During operation, a user activates pump 130 to remove cooling fluid from fluid source 120 and deliver it into inflow section 212 of conduit 210. The operator can also activate electrosurgical generator 110 to supply energy to surgical instrument 140. The energy supplied by electrosurgical generator 140 travels through conductor 220 and reaches surgical instrument 140. At this point, the electrosurgical energy accumulates heat as a consequence of the energy delivered thereto.

As discussed hereinabove, the operator of electrosurgical system 100 can activate pump 130 to supply cooling fluid to surgical instrument 140. After pump 130 is activated, the cooling fluid starts flowing through inflow section 212 of conduit 210. The activation of pump 140 may cause a portion of inflow section 212 to move within walls 232 of path 230. The movement of inflow section 212 may follow first and second trails 238, 240 within housing 204 of cartridge 100. During the movement of inflow section 212 of conduit 210, a portion of inflow section 212 may positioned itself in chamber 234.

Though a portion of inflow section 212 may move in response to fluid being pumped through conduit 210, it is envisioned that conduit fitting 216 does not move within housing 204 of cartridge 100. Conduit fitting 216, as discussed above, interconnects first portion 212a and second portion 212b of inflow section 212 of conduit 210. Rib walls 236 axially fix conduit fitting 216 in place. Since rib walls 236 axially secure conduit fitting 216, conduit fitting 216 may remain in its original position after the user activates pump 130. The remaining portions of inflow section 212 of conduit 210, however, may still move when a user starts pump 130.

Irrespective of the movement of inflow section 212, the cooling fluid initially stored in fluid source 120 travels through inflow section 212 of conduit 210 and eventually reaches surgical instrument 140. As the cooling fluid reaches surgical instrument 140, heat is transferred from surgical instrument 140 to the cooling fluid. Thereafter, the cooling fluid travels through outflow section 214 of conduit 210 away from surgical instrument 140 and into housing 204 of cartridge 100. Outflow section 214 of conduit 210, and thus the fluid, exits housing 204 through opening 205 of cartridge 200.

Although the present disclosure describes specific embodiments, these embodiments should not be construed as limitations on the present disclosure, but merely exemplifications of the embodiments of the present disclosure. Those skilled in the art will envision many other variations that are within the scope and spirit of the present disclosure as defined by the claims appended thereto.

What it is claimed is:

1. An electrosurgical system, comprising:
    a surgical instrument including:
        a handle portion; and
        a shaft portion extending distally from the handle portion;
    a generator;
    a fluid source;
    a cartridge for interconnecting the generator and the fluid source to the surgical instrument, wherein the cartridge is spaced apart from the handle portion of the surgical instrument and wherein the cartridge includes:
        a housing defining a first opening therein, a second opening therein, and a third opening therein;
        an inflow section extending between the first opening and the second opening to carry fluid from the fluid source to the surgical instrument;
        a first wall and a second wall each disposed within the housing and extending side by side to define a first passageway therebetween having a first portion of the inflow section disposed therein;
        an outflow section extending between the first opening and the second opening to carry fluid from the surgical instrument to the fluid source, wherein the inflow section and the outflow section are in fluid communication with one another and extend in substantially opposing directions at the first opening;
        and a conductor extending between the second opening and the third opening, the conductor configured to transmit energy from the generator to the surgical instrument;
        wherein each of the inflow section, the outflow section, and the conductor extends through the second opening.

2. The electrosurgical system of claim 1, wherein the housing of the cartridge defines a chamber located centrally therein, the chamber having a second portion of the inflow section disposed therein.

3. The electrosurgical system of claim 2, wherein the chamber is configured to allow slack in the portion of the inflow section.

4. The electrosurgical system of claim 1, wherein the inflow section includes:
    a first end connected to the surgical instrument;
    an intermediate portion disposed within the cartridge; and
    a second end connected to the fluid source.

5. The electrosurgical system of claim 1, wherein the cartridge includes a third wall disposed within the housing and extending side by side with the second wall to define a second passageway therebetween having a portion of the outflow section disposed therein.

6. The electrosurgical system of claim 5, wherein the first wall has an end and the third wall has an end, the first opening defined between the end of the first wall and the end of the third wall.

7. The electrosurgical system of claim 6, wherein the end of the first wall and the end of the second wall are aligned.

8. The electrosurgical system of claim 5, wherein the cartridge includes a fourth wall disposed within the housing between the conductor and the inflow section to separate the inflow section from the conductor.

9. The electrosurgical system of claim 8, wherein the cartridge includes a fifth wall disposed within the housing and extending side by side with the fourth wall to define a third passageway therebetween having the conductor disposed therein.

10. The electrosurgical system of claim 1, wherein the first portion of the inflow section is slidably disposed within the first passageway.

11. The electrosurgical system of claim 2, wherein the second wall has a U-shaped portion that defines the chamber therein.

12. The electrosurgical system of claim 1, wherein the handle portion is configured to be held in a pistol-grip fashion.

13. The electrosurgical system of claim 1, wherein the first opening is defined through a first lateral side of the housing and the third opening is defined through a second lateral side of the housing disposed opposite the first lateral side.

14. The electrosurgical system of claim 1, wherein at least a portion of the second wall has a serpentine configuration configured to guide the inflow section along a serpentine pathway.

* * * * *